(12) United States Patent
Zeppezauer et al.

(10) Patent No.: US 8,778,875 B2
(45) Date of Patent: Jul. 15, 2014

(54) USE OF AN ACTIVE BIOLOGICAL SUBSTANCE IN ABNORMAL CELLULAR AND VIRAL MEMBRANE PHYSIOLOGIES

(75) Inventors: Michael Zeppezauer, Saarbrücken (DE); Peter Gross, Bexbach (DE)

(73) Assignee: Symbiotec Gesellschaft zur Forshung und Entwickling auf dem Gebiet der Biotechnologie, mbH, Saarbrucken (DE)

( * ) Notice: Subject to any disclaimer, the term of this patent is extended or adjusted under 35 U.S.C. 154(b) by 1329 days.

(21) Appl. No.: 11/989,784

(22) PCT Filed: Aug. 4, 2006

(86) PCT No.: PCT/EP2006/007764
§ 371 (c)(1),
(2), (4) Date: Jul. 23, 2009

(87) PCT Pub. No.: WO2007/017212
PCT Pub. Date: Feb. 15, 2007

(65) Prior Publication Data
US 2009/0304597 A1    Dec. 10, 2009

(30) Foreign Application Priority Data
Aug. 5, 2005    (DE) .................. 10 2005 037 602

(51) Int. Cl.
*A61K 38/00*    (2006.01)
*A61K 38/16*    (2006.01)
*A61K 38/17*    (2006.01)

(52) U.S. Cl.
USPC .......................................... 514/3.7; 514/21.2

(58) Field of Classification Search
None
See application file for complete search history.

(56) References Cited

U.S. PATENT DOCUMENTS

| | | | | |
|---|---|---|---|---|
| 4,818,763 A | * | 4/1989 | Rusch et al. | 514/9.7 |
| 5,182,257 A | * | 1/1993 | Zeppezauer et al. | 514/19.3 |
| 5,578,571 A | * | 11/1996 | Zeppezauer et al. | 514/19.3 |
| 5,714,462 A | * | 2/1998 | Davies et al. | 514/3.9 |
| 5,753,789 A | * | 5/1998 | Chu et al. | 536/24.5 |
| 5,780,432 A | * | 7/1998 | Zeppezauer et al. | 514/19.3 |
| 6,565,854 B2 | * | 5/2003 | Class et al. | 424/234.1 |
| 6,884,423 B1 | * | 4/2005 | Class et al. | 424/234.1 |
| 7,902,146 B2 | * | 3/2011 | Zeppezauer et al. | 514/19.6 |
| 2004/0219140 A1 | * | 11/2004 | Class et al. | 424/94.61 |
| 2007/0110768 A1 | * | 5/2007 | Class | 424/204.1 |

OTHER PUBLICATIONS

Carrillo-Infante et al. (2007, Int. J. Oncol. 30:1521-1528).*
Izzo et al., 2008, Biol. Chem. 389: 333-343.*
Class et al. (1996, Cellular and Molecular Biology 42:S25-S26).*

* cited by examiner

*Primary Examiner* — Elizabeth C Kemmerer
(74) *Attorney, Agent, or Firm* — One3 IP Management, PC; Dean G. Stathakis; Peter D. Weinstein

(57) ABSTRACT

An active biological substance is disclosed for use in abnormal cellular and viral membrane physiologies in human and mammal organisms. The active substance has diagnostic and/or therapeutic properties and contains or consists of at least one component selected from the group of substances including: histones, covalently modified histones, histone-like polypeptides, biologically active histone sequences and histone-like polypeptides as agents for stopping the supply to solid tumors over their blood vessels, for killing cells infected by virus and for killing tumour cells with disturbed lipid asymmetry.

11 Claims, No Drawings

USE OF AN ACTIVE BIOLOGICAL SUBSTANCE IN ABNORMAL CELLULAR AND VIRAL MEMBRANE PHYSIOLOGIES

The invention relates to the use of an active biological substance for medical purposes in abnormal cellular and viral membrane physiologies.

Eukaryotic cell membranes are known to consist of proteins, carbohydrates and especially lipids, mainly cholesterol and also phospholipids and glycosphingolipids.

The phospholipids are known to consist of sphingomyelin (SM) and of the phospholipids phosphatidylcholine (PC), phosphatidylethanolamine (PE) and phosphatidylserine (PS). Small amounts of other phospholipids also exist.

The ratios by quantity of the cell membrane building blocks differ in humans and in various mammal species.

A cellular membrane consists of an outer layer and an inner layer. Cellular regulation processes ensure that the respective phospholipid compositions are maintained in each layer. The phospholipid compositions in the outer and inner layers are different. The phospholipids PE and PS occur mainly in the inner layers, while the phospholipids PC and SM occur in both layers of the cell membrane. These vertical lipid asymmetries in the outer and inner cell membrane layers are strictly regulated in every eukaryotic cell. However, the cell membrane regulation in each cell is effected by different enzymes and transport proteins, which ensure that the predetermined proportions of the individual lipid components in the outer and inner layers are permanently maintained and that the vertical lipid asymmetry predetermined for a healthy cell remains undisturbed.

Of particular note is the ATP-driven transport of the aminophospholipids PE and PS by amino-phospholipid translocase (APLT) from the outer layers into the inner layers of the cell membrane, such that, in healthy cells, it is possible to ensure permanently that the phospholipids PE and PS are maintained at the predetermined proportions in the inner layer.

This applies also to the endothelial cells of normal blood vessels, the outer layers of which delimit the inner face of the blood vessel walls.

If the milieu of healthy cells becomes pathologically altered, the regulation system of the healthy cells for maintaining the predetermined lipid asymmetries in the bilayers of the cell membranes may become impaired. The continuous ATP-driven transport of the phospholipids PE and PS from the outer layers into the inner layers of the cell membranes is no longer guaranteed if the healthy cells, e.g. healthy endothelial cells of blood vessels, are located in the vicinity of tumor cells. The high growth rate of a solid tumor leads to an abnormal metabolic situation in tumors, which situation is caused inter alia by oxygen deficiency and free oxygen radicals. Several factors lead to dysregulation of the lipid asymmetry in the membranes of tumor cells. The dysregulation also carries over to the endothelial cells adjacent to the tumor cells, as has been confirmed by experimental studies.

In addition to a pathologically disturbed cell milieu, which may possibly lead to disturbance of the lipid symmetry in the layers of the cell membranes, such disturbance may also be caused by viruses, e.g. retroviruses, that have penetrated into cells.

A disturbed lipid symmetry in the layers of cell membranes is found when anionic lipid constituents are present in considerable numbers in the outer layers of the cell membranes of cells, which are referred to below as pathogenic and may have a malignant potential. The anionic lipid constituents particularly involve phosphatidylserine (PS).

Abnormal cells of this kind, with pathologically disturbed vertical lipid asymmetries in the cell membrane layers, are to be found in serious diseases. Among these are diseases involving solid tumors.

Pathological cells with disturbed lipid asymmetries in the bilayers of their cell membranes are often not detected in good time, because of the lack of early diagnosis, which is why surgical interventions followed by chemotherapy and/or radiotherapy are needed after a disease has become manifest, e.g. with solid tumors. After such an operation, the patients are often left at risk of a renewed outbreak of the disease, since not all pathological cells have been able to be removed or killed off. In the patients affected, it is therefore possible that at some time cancer cells will be able to develop again from the remaining pathogeneic cells, in which case the renewed outbreak of the disease is often no longer treatable, since conventional chemotherapy and radiation procedures of the kind used to treat the initial outbreaks of the disease often fail when used to treat the renewed outbreak of the disease, or they can no longer be tolerated by the patients because of their weakened condition.

A renewed outbreak of a disease, however, would be avoidable with an active substance that can diagnose pathological cells and kill them off before they are able to manifest themselves outwardly as a cancerous disease.

Experimental studies have also shown that eukaryotic cells infected by viruses have pathologically disturbed vertical lipid asymmetries in the cell membranes, e.g. in AIDS and in hepatitis C.

The viruses that infect cells also include enveloped viruses, in which the viral envelopes are derived from the membranes of their host cells.

Viruses can be classed in various virus families according to various main criteria (nature and shape of the genome, form of symmetry of the capsids, and the presence of a membrane shell). The viruses with membrane shells (viral envelopes) include the virus families below:

Flaviviridae
Togaviridae
Coronaviridae
Arteriviridae
Rhabdoviridae
Paramyxoviridae
Filoviridae
Bornaviridae
Orthomyxoviridae
Bunyaviridae
Arenaviridae
Retroviridae
Hepadnaviridae
Herpesviridae
Poxviridae
Asfarviridae In virus morphogenesis, after the replication processes of the enveloped viruses in their host cells, parts of the cellular membrane systems of the host cells are integrated into the viral envelopes of the viruses, such that the distrurbed lipid asymmetries of the cellular membrane parts are carried over into the viral envelopes. It is in this sense that the expression "abnormal viral membrane physiology" is also to be understood here.

European patent 0149486 has disclosed the use of at least one histone and/or at least one active histone section for diagnosis and for immunotherapy, for treatment of endocrinological disturbances, and for cancer therapy.

European patent 0392315 has supplemented the above prior art by disclosing that histone H1 in particular, or its active section, is suitable for cancer therapy.

European patent 0438756 and U.S. Pat. No. 5,780,432 have further disclosed a medicament consisting of a cytostatic as a first active substance and of a histone, or its active section, as a second active substance, which active substances together exert a synergistic effect in cancer therapy and in the treatment of autoimmune diseases.

German patent application DE 197 15 149 A1 and the PCT application with the international publication number WO 98/46252 disclose a therapeutic agent based on histone H1 or histone-like proteins or active parts thereof for the treatment of cancer cells, in particular of the hematogenic system, which have, as receptors, cell-membrane-resistant core histones or core-histone-like polypeptides. The therapeutic histone H1 active substance can also be a recombinant H1 subtype.

From J. J. Killian et al. in the journal Emerging Therapeutic Targets (1999) 3 (3), pages 454-468, "Cell Membrane Lipids as Experimental Therapeutic Targets" and from S. Ran et al. in the journal Clin. Cancer Dis. 2005, Feb. 15, 11 (4): 1551-62 "Antitumor Effects of a Monoclonal Antibody that binds Anionic Phospholipids on the Surface of Tumor Blood Vessels in Mice", it is known that anionic phospholipids, in particular phosphatidylserine, serve as targets for monoclonal antibodies in endothelial cells of tumor vessels in mice, with the aim of destroying the tumors by suppressing the supply of blood.

In European patent application 04011015.7 of May 7, 2004, it has already been proposed by us to use the active substance according to the invention in particular for early diagnosis and/or preventive treatment of virus-infected living cells, its efficacy being directed selectively against cell membranes, particularly phospholipid membranes of virus-infected cells, that are modified after the virus attack to act as an identifer of the virus attack, and also have histones in the cell membranes which, in healthy cells not infected by viruses, have hitherto only been identifiable in the nucleus.

From H. Zhao, K. J. Kinnunen et al. in the journal Biochemistry 2004, 43; 10192-10202 "Interactions of Histone H1 with Phospholipids and Comparison of its Binding to Giant Liposomes and Human Leukemic T-cells", it is known that bovine histone H1 binds to phosphatidylserine of liposomes and leukemic T-cells and then destroys these.

The object of the invention is to make available a medical active substance which not only has an identifier function in respect of disease with solid tumors and/or in respect of viral disease in humans and mammals or in respect also of latent diseases of this kind, but at the same time also has a cytostatic or virostatic action potential for destroying pathogenic cells with disturbed lipid asymmetry, as is characteristic for cells infected by viruses and, in solid tumors, both for the tumor cells and also for the endothelial cells of the blood vessels supplying the tumors.

The invention starts out from the recognition that the membranes of pathogenic cells, in particular cells of solid tumors and/or cells infected by viruses, have a disturbed asymmetry of the lipid composition in the membrane bilayers, characterized by increased presence of anionic phospholipids, in particular phosphatidylserine, in the outer layer of the membranes.

According to the invention, the object is achieved by an active biological substance having diagnostic and/or therapeutic properties and containing or consisting of at least one component selected from the group of substances including:
histones,
covalently modified histones,
histone-like polypeptides,
biologically active sequences of histones and histone-like polypeptides,
as agents
for stopping supply to solid tumors via their blood vessels,
for killing off cells infected by viruses,
in abnormal cellular and/or viral membrane physiologies caused by defective regulation of the phospholipids in the outer cellular membrane areas.

Advantageous developments of the invention are set forth in the subclaims and in the following description of advantageous examples of use.

The cellular membranes of solid tumors, but also the endothelial cells of the blood vessels supplying the solid tumors especially to meet their increased oxygen demand, have, like the tumors too, a pathologically disturbed membrane physiology, attributable to defective regulation, suppression of anionic phospholipids, in particular phosphatidylserine, in the outer membrane layers.

The active substance according to the invention can therefore be used to damage the endothelial cells of blood vessels that supply the solid tumors. For example, recombinant human histone rH1.3 is used as active substance according to the invention. The invention is not limited to this, and, accordingly, it is also possible for other H1 subtypes H1.0, H1.1, H1.2, H1.4, H1.6, H1.t and H1.x and their biologically active sections, but also the core histones, to be used according to the invention as active substance.

Histone as active substance can be used in therapeutic doses of, for example, $10^{-1}$ to $10^{-2}$ µM substantially without side effects on the organism and its immune system.

Histone rH1.3 as a diagnostic and at the same time therapeutic substance is conveyed through the blood stream into the blood vessels of tumors in a patient suffering from solid tumors. In the blood vessels, the active substance attacks the outsides of the membranes of the endothelial cells that form the inner walls of the pathological blood vessels in or on the solid tumors.

As the histone (H1) used as active substance binds to phosphatidylserine (PS) and/or to membrane histones of the enothelial cells, the substantially unordered structure of H1 changes to an ordered structure H1α with α-helix components (amphipathic helix), which can be illustrated as follows

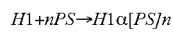

This results in an m-fold self-aggregation of H1a, which can be further characterized by the relationship

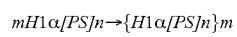

The self-aggregations of the histones (here H1) on the membranes of the endothelial cells of the tumor blood vessels leads to apoptosis and to pore formation in the endothelial cell membranes, which leads to destruction of the endothelial cells. This continuing process of destruction on a large number of endothelial cells finally leads to massive vessel damage and therefore decreases the supply of oxygen and nutrients to the solid tumors.

The active substance according to the invention binds not only to the membranes of the endothelial cells of blood vessels on or in the interior of tumors, but also binds to the membranes of virus-infected cells which, on account of the virus attack, have a disturbed lipid asymmetry in their bilayers.

Finally, the active substance according to the invention opens up new diagnostic and therapeutic possibilities in respect of cells that are infected by viruses and that can be reached by the active substance especially, but not exclusively, via body fluids. The lysis of the virus-infected cells, even before release of the viruses from their host cells, means that these can be identified by the abnormal lipid asymmetries of the lipid double membranes of the host cells for the active substance according to the invention, which, alone or in combination with cytostatics and/or virostatics, destroys the virus-infected host cells and thus prevents replication of the viruses.

In many cases, a concentration of the active substance, e.g rH1.3, of $10^{-1}$ to $10^2$ μM is sufficient.

Since the active substance according to the invention crosses the blood/brain barrier by itself and also as a vehicle for cytostatics and virostatics, this also opens up new diagnostic or therapeutic possibilities for treatment of diseases in the brain, particularly for early diagnosis of brain cells that have an abnormal lipid asymmetry in the lipid double membrane.

The invention claimed is:

1. A method of treating a viral infection associated with cells having a disturbed lipid asymmetry in a membrane bilayer, the method comprising the step of administering an active biological substance to a mammal suffering from the viral infection,
    wherein the active biological substance is histone H1.3,
    wherein the viral infection is Epstein Barr virus (EBV) infection, and
    wherein administration of the active biological substance destroys the cells having a disturbed lipid asymmetry in a membrane bilayer, thereby treating the viral infection in the mammal.

2. The method according to claim 1, wherein the active biological substance is administered in conjunction with cytostatics and/or virostatics for combined therapy.

3. The method according to claim 1, wherein the mammal is a human.

4. The method according to claim 1, wherein the disturbed lipid asymmetry includes an increased presence of anionic phospholipids in the outer layer of the membrane.

5. The method according to claim 4, wherein the anionic phospholipids include phosphatidylserine.

6. A method of diagnosing cells infected with a virus, the method comprising the steps of:
    administering an active biological substance to a mammal suspected of having a viral infection, wherein cells infected with the virus have a disturbed lipid asymmetry in a membrane bilayer, wherein administration of the active biological substance lyses cells having a disturbed lipid asymmetry in a membrane bilayer, and wherein the active biological substance is histone H1.3 and wherein the viral infection is Epstein Barr virus (EBV) infection and
    detecting the presence of lysed cells, wherein the presence of lysed cells is indicative of cells infected with a virus.

7. The method according to claim 6, wherein the active biological substance is used in conjunction with a marker molecule for diagnostic purposes.

8. The method according to claim 6, wherein the active biological substance is administered in conjunction with cytostatics and/or virostatics for combined therapy.

9. The method according to claim 6, wherein the mammal is a human.

10. The method according to claim 6, wherein the disturbed lipid asymmetry includes an increased presence of anionic phospholipids in the outer layer of the membrane.

11. The method according to claim 10, wherein the anionic phospholipids include phosphatidylserine.

* * * * *